(12) United States Patent
Chen

(10) Patent No.: US 8,570,496 B2
(45) Date of Patent: Oct. 29, 2013

(54) OPTICAL DETECTION APPARATUS AND OPTICAL MEASUREMENT SYSTEM

(75) Inventor: Chao-Ming Chen, Hsinchu (TW)

(73) Assignee: Lite-On It Corporation, Taipei (TW)

( * ) Notice: Subject to any disclaimer, the term of this patent is extended or adjusted under 35 U.S.C. 154(b) by 75 days.

(21) Appl. No.: 13/307,004

(22) Filed: Nov. 30, 2011

(65) Prior Publication Data

US 2013/0100434 A1    Apr. 25, 2013

(30) Foreign Application Priority Data

Oct. 20, 2011    (TW) ............................... 100138070 A

(51) Int. Cl.
*G01N 33/48* (2006.01)
*G01N 33/49* (2006.01)

(52) U.S. Cl.
CPC .................................... *G01N 33/49* (2013.01)
USPC .......................................................... 356/39

(58) Field of Classification Search
CPC ............................. G01N 33/48; G01N 33/49
USPC .................................................... 356/39–42
See application file for complete search history.

(56) References Cited

U.S. PATENT DOCUMENTS

| | | | |
|---|---|---|---|
| 4,727,033 A * | 2/1988 | Hijikata et al. ................. 436/69 |
| 5,265,169 A * | 11/1993 | Ohta et al. ..................... 382/130 |
| 5,473,706 A * | 12/1995 | Bacus et al. ................... 382/133 |
| 8,248,586 B2 * | 8/2012 | Tomita ............................ 356/39 |
| 2008/0144004 A1 * | 6/2008 | Rosenthal ....................... 356/39 |
| 2010/0259747 A1 * | 10/2010 | Sekimoto ........................ 356/39 |

* cited by examiner

*Primary Examiner* — Michael P Stafira
(74) *Attorney, Agent, or Firm* — Jianq Chyun IP Office

(57) ABSTRACT

An optical detection apparatus which is capable of measuring a sample is provided. The optical detection apparatus includes a plurality of light emission units, a light receiving unit, a driving unit, and an analyzing unit. Each of the light emission units is capable of emitting a light beam. The light receiving unit is capable of receiving the light beam passing through the sample and is capable of converting the received light beam to an electrical signal. The driving unit is capable of changing the relative position of the light emission units and the sample. The analyzing unit is electrically connected to the light receiving unit and is capable of measuring a property of the sample by using the electrical signal. A number of the light receiving unit is less than a number of the light emission units. An optical measurement system including the optical detection apparatus is also provided.

11 Claims, 2 Drawing Sheets

OPTICAL DETECTION APPARATUS AND OPTICAL MEASUREMENT SYSTEM

CROSS-REFERENCE TO RELATED APPLICATION

This application claims the priority benefit of Taiwan application Ser. No. 100138070, filed on Oct. 20, 2011. The entirety of the above-mentioned patent application is hereby incorporated by reference herein and made a part of this specification.

BACKGROUND OF THE INVENTION

1. Field of the Invention

The present invention generally relates to an optical apparatus, in particular, to an optical detection apparatus and an optical measurement system.

2. Description of Related Art

In order to intercept straight light to obtain the maximum light utilization efficiency, conventional multi-light source optical measurement systems mostly adopt a design in which the light emission units and the light receiving units are disposed in pairs. However, in the conventional multi-light source optical measurement system, the light emission unit and the light receiving unit need to be paired, so the manufacturing cost cannot be reduced. Moreover, each of the light receiving units needs an analyzing circuit; consequently, the electrical circuits in the multi-light source optical measurement system are hard to be simplified.

Further, in the conventional multi-light source optical measurement system, to avoid the light receiving unit from being affected by stray light of a single light emission unit or different light emission units, a shielding structure is disposed between each pair of the light emission unit and the light receiving unit or disposed on each light receiving unit. However, the shielding structures also increase the manufacturing cost and design difficulty of the multi-light source optical measurement system.

SUMMARY OF THE INVENTION

Accordingly, the present invention is directed to an optical detection apparatus and an optical measurement system, which have low manufacturing cost.

The present invention provides an optical detection apparatus capable of measuring a sample. The optical detection apparatus includes a plurality of light emission units, a light receiving unit, a driving unit, and an analyzing unit. Each of the light emission units is capable of emitting a light beam. The light receiving unit is capable of receiving the light beam passing through the sample and is capable of converting the light beam passing through the sample to an electrical signal. The driving unit is capable of changing the relative position of the light emission units and the sample. The analyzing unit is electrically connected to the light receiving unit and is capable of measuring a property of the sample by using the electrical signal. A number of the light receiving unit is less than a number of the light emission units.

The present invention provides an optical measurement system, which includes the optical detection apparatus described above and a carrier. The carrier has at least one accommodation groove, and the accommodation groove is capable of accommodating a sample.

In an embodiment of the present invention, the light emission units are arranged into a straight line along a row direction. The driving unit is capable of moving the light emission units back and forth along the row direction when positions of the sample and the light receiving unit are fixed.

In an embodiment of the present invention, the light emission units are arranged into an annular shape. The driving unit is capable of rotating the light emission units along the annular shape when positions of the sample and the light receiving unit are fixed.

In an embodiment of the present invention, the sample includes blood.

In an embodiment of the present invention, the property of the sample measured by using the electrical signal includes absorbance of the sample.

Based on the above, the optical detection apparatus and the optical measurement system of the present invention use the driving unit to change the relative position of the light emission units and the sample, thereby enabling the light beams emitted by the light emission units to pass through the sample sequentially. Therefore, the optical detection apparatus and the optical measurement system of the present invention do not need the design in which the light emission units and the light receiving units are disposed in pairs. In other words, in the optical detection apparatus and the optical measurement system of the present invention, the number of the light receiving unit is less than the number of the light emission units, so as to reduce the number of the light receiving unit, thereby effectively reducing the manufacturing cost of the optical detection apparatus and the optical measurement system.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Figure 1:
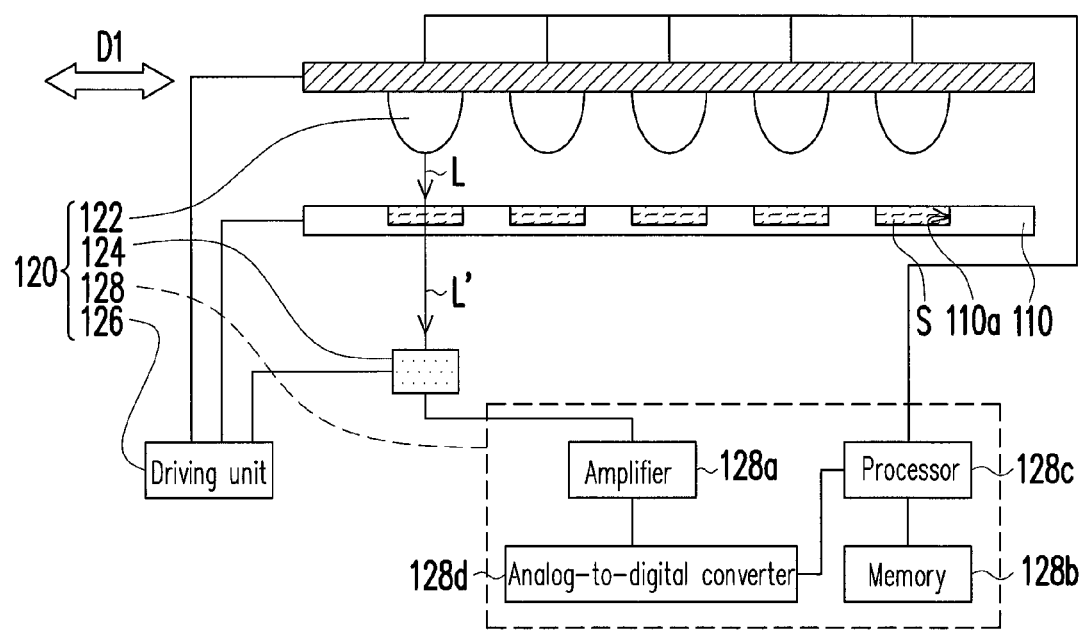
FIG. 1 is a schematic view of an optical measurement system according to a first embodiment of the present invention.

Reference will now be made in detail to the present embodiments of the invention, examples of which are illustrated in the accompanying drawings. Wherever possible, the same reference numbers are used in the drawings and the description to refer to the same or like parts.

First Embodiment

FIG. 1 is a schematic view of an optical measurement system according to a first embodiment of the present invention. Referring to FIG. 1, an optical measurement system 100 of this embodiment includes a carrier 110 and an optical detection apparatus 120. The carrier 110 has a plurality of accommodation grooves 110a. The accommodation groove 110a is capable of accommodating a sample S. In this embodiment, the sample S is, for example, blood. In this embodiment, the accommodation groove 110a is preferably made of a material having high light transmittance and low biological reactivity, for example, polymethyl methacrylate, (PMMA), polydimethyl siloxane (PDMS), or polycarbonate (PC). However, the present invention is not limited to this.

The optical detection apparatus 120 in this embodiment includes a plurality of light emission units 122, at least one light receiving unit 124, a driving unit 126, and an analyzing unit 128. Each light emission unit 122 is capable of emitting a light beam L. The light emission unit 122 in this embodiment is, for example, a light emitting diode (LED). However, the present invention is not limited to this, and in other embodiments, the light emission unit 122 may also be a laser or a xenon lamp.

It should be noted that, in this embodiment, wavelength bands of light beams L emitted by at least two light emission units 122 among the light emission units 122 may be different. For example, the wavelength band of the light beam L emitted by one of the light emission units 122 is substantially 450 nm, and the wavelength band of the light beam L emitted by another of the light emission units 122 is substantially 500 nm. Alternatively, the wavelength band of the light beam L emitted by one of the light emission units 122 is substantially 500 nm, and the wavelength band of the light beam L emitted by another of the light emission units 122 is substantially 600 nm. However, the present invention is not limited to this, the wavelength bands of the light beams L emitted by the light emission units 122 may be designed properly according to actual requirements, and even the wavelength bands of the light beams L emitted by the light emission units 122 may be different from one another to meet the requirements of actual measurement.

The driving unit 126 in this embodiment is capable of changing the relative position of the light emission units 122 and the sample S. For example, the driving unit 126 may move the positions of the light emission units 122 when positions of the light receiving unit 124 and the sample S are fixed, or move the position of the light receiving unit 124 when positions of the light emission units 122 and the sample S are fixed.

More specifically, in this embodiment, the light emission units 122 may be arranged into a straight line along a row direction D, and the driving unit 126 moves the light emission units 122 along the row direction D when the positions of the sample S and the light receiving unit 124 are fixed. Alternatively, the driving unit 126 may move the light receiving unit 124 along a direction opposite to the row direction D when the positions of the light emission units 122 and the sample S are fixed. In this way, the light beams L having different wavelength bands may pass through the sample S sequentially and then be received by the light receiving unit 124, so as to provide the information for the analyzing unit 128 to analyze the property of the sample S. The driving unit 126 in this embodiment may be a step motor, a servo motor, a linear motor, a DC brushless motor, a DC brush motor, or an induction motor, which is not limited in the present invention.

The light receiving unit 124 in this embodiment is capable of receiving a light beam L' passing through the sample S, and converting the light beam L' passing through the sample S to an electrical signal. In this embodiment, the light receiving unit 124 is, for example, a photodiode. However, the present invention is not limited to this, and in other embodiments, the light receiving unit 124 may also be a photo-multiplier tube (PMT) or a charge-coupled device (CCD).

The analyzing unit 128 in this embodiment is electrically connected to the light receiving unit 124 and is capable of measuring the property of the sample S by using the electrical signal converted from the light beam L'. More specifically, the analyzing unit 128 includes an amplifier 128a, an analog-to-digital converter 128d, a processor 128c, and a memory 128b. The amplifier 128a amplifies the electrical signal generated by the light receiving unit 124. The analog-to-digital converter 128d converts the analog electrical signal to a digital electrical signal. The processor 128c measures the property of the sample S by using the digital electrical signal. The memory 128b stores a value of the electrical signal to measure the property of the sample S and stores the measured property of the sample S. The measured property of the sample S may be displayed through a screen or be printed for an operator to know the information of the sample property, such as component compositions and concentration. In this embodiment, the processor 128c measures absorbance of the sample S to determine concentration of specific components in the sample S.

It should be noted that, the driving unit 126 is capable of changing the relative position of the light emission units 122 and the sample S, so as to enable the light beams L emitted by the light emission units 122 to pass through the sample S sequentially, and therefore, the optical measurement system 100 of this embodiment does not need the design of the conventional optical measurement system in which the light emission units and the light receiving units are disposed in pairs. In other words, in the optical measurement system 100 of this embodiment, a number of the light receiving unit 124 may be less than a number of the light emission units 122. For example, the optical measurement system 100 of this embodiment may include only one light receiving unit 124 and a plurality of light emission units 122, or include two light receiving units 124 and a plurality of light emission units 122. In this way, the manufacturing cost of the optical measurement system 100 of this embodiment may be reduced significantly due to the reduction of the light receiving unit 124.

In this embodiment, the light emission unit 122 emits the light beam L only when the emission unit 122 is substantially aligned with the light receiving unit 124. In other words, when one of the light emission units 122 is substantially aligned with the light receiving unit 124, the light emission unit 122 aligned with the light receiving unit 124 then emits the light beam L, and other light emission units 122 do not emit any light beam L. In this way, the light emission units 122 having different wavelength bands will not interfere with one another, thereby improving the measurement precision of the optical measurement system 100 in this embodiment. In addition, the optical measurement system 100 of this embodiment may also omit the shielding structure in the conventional optical measurement system, thereby further reducing the manufacturing cost of the optical measurement system 100.

Second Embodiment

Figure 2:
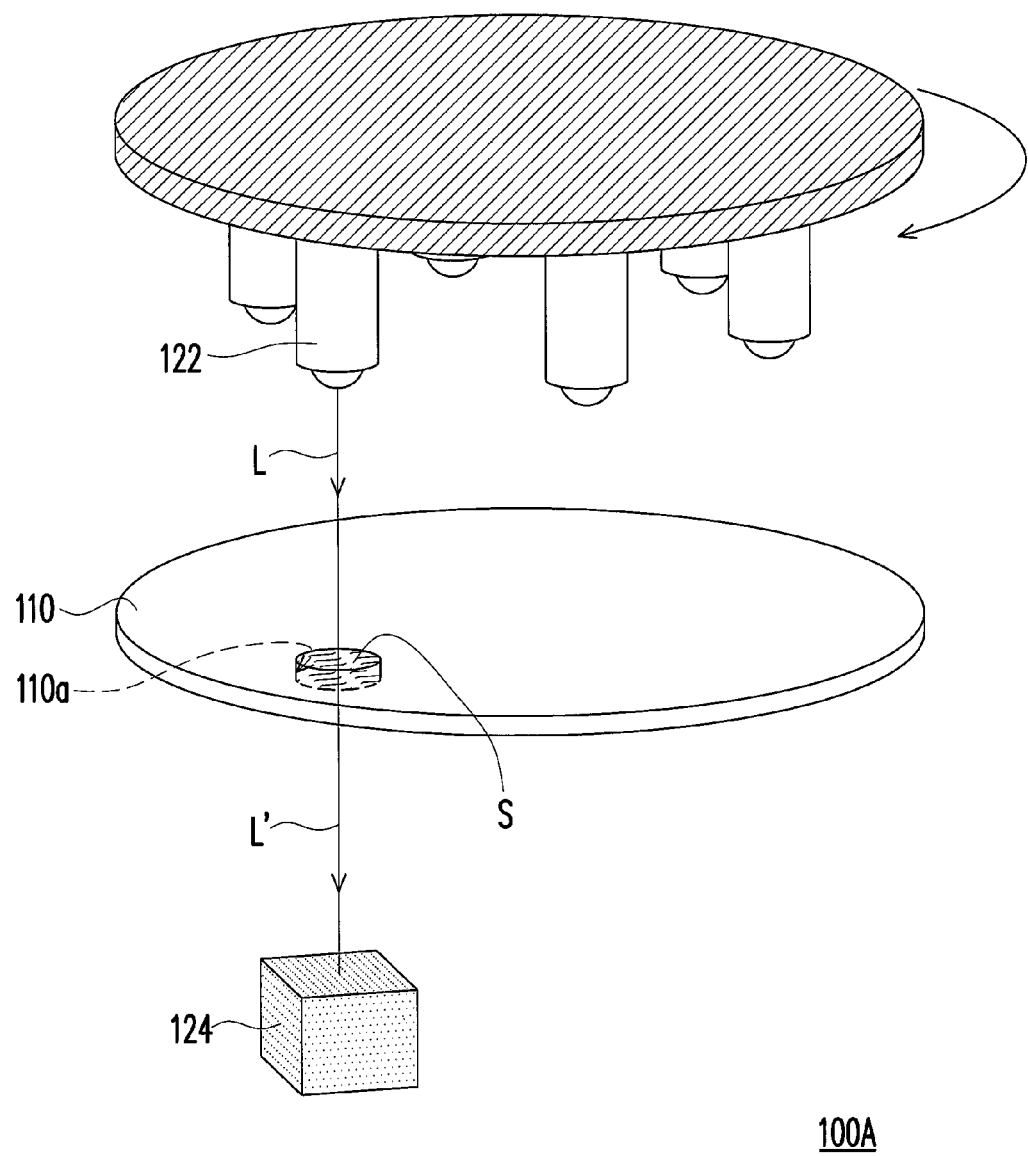
FIG. 2 is a schematic view of an optical measurement system according to a second embodiment of the present invention.

FIG. 2 is a schematic view of an optical measurement system according to a second embodiment of the present invention. Referring to FIG. 2, an optical measurement system 100A of this embodiment is similar to the optical measurement system 100 of the first embodiment, and therefore, the same elements are marked with the same reference numerals. The optical measurement system 100A in this embodiment is different from the optical measurement system 100 in the first embodiment in the following aspects: the arrangement of the light emission units 122, the manner for the driving unit 126 to change the relative position of the light emission units 122 and the sample S, and a number of accommodation grooves 110a in the carrier 110. The differences between the two embodiments are illustrated below, and the same elements are not repeated herein.

In this embodiment, the light emission units 122 may arrange into an annular shape, and the driving unit 126 may rotate the light emission units 122 clockwise or anticlockwise along the annular shape when positions of the sample S and the light receiving unit 124 are fixed, as shown by arrows in FIG. 2. Alternatively, the driving unit 126 may rotate the light receiving unit 124 clockwise or anticlockwise along the annular shape when positions of the light emission units 122 and the sample S are fixed. In this way, light beams L having different wavelength bands may pass through the sample S sequentially to be received by the light receiving unit 124, so as to provide the information for the analyzing unit 128 to analyze the property of the sample S. In addition, the carrier 110 in this embodiment may have only one accommodation groove 110a, and definitely, the number of the accommodation groove is not limited herein.

The optical measurement system 100A in this embodiment has similar efficacy and advantages with the optical measurement system 100 in the first embodiment, which are not repeated herein.

In view of the above, in the optical detection apparatus and the optical measurement system according to the embodiments of the present invention, the driving unit is capable of changing the relative position of the light emission units and the sample, so that the light beams emitted by the light emission units may pass through the sample sequentially and be received by the light receiving unit, and therefore, the optical detection apparatus and the optical measurement system according to the embodiments of the present invention do not need the design of the prior art in which the light emission units and the light receiving units are disposed in pairs. In other words, the optical detection apparatus and the optical measurement system according to the embodiments of the present invention may reduce the number of configured light receiving units, thereby effectively reducing the manufacturing cost of the optical measurement system.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. An optical detection apparatus, capable of measuring a sample, the optical detection apparatus comprising:
a plurality of light emission units, each capable of emitting a light beam;
at least one light receiving unit, capable of receiving the light beam passing through the sample, and converting the light beam passing through the sample to an electrical signal;
a driving unit, capable of changing the relative position of each of the light emission units and the sample; and
an analyzing unit, electrically connected to the light receiving unit, and capable of measuring a property of the sample by using the electrical signal, wherein a number of the light receiving unit is less than a number of the light emission units,
wherein the light emission units are arranged into a straight line along a row direction, and the driving unit is capable of moving the light emission units back and forth along the row direction when positions of the sample and the light receiving unit are fixed.

2. An optical detection apparatus, capable of measuring a sample, the optical detection apparatus comprising:
a plurality of light emission units, each capable of emitting a light beam;
at least one light receiving unit, capable of receiving the light beam passing through the sample, and converting the light beam passing through the sample to an electrical signal;
a driving unit, capable of changing the relative position of each of the light emission units and the sample; and
an analyzing unit, electrically connected to the light receiving unit, and capable of measuring a property of the sample by using the electrical signal, wherein a number of the light receiving unit is less than a number of the light emission units, wherein when one of the light emission units is substantially aligned with the light receiving unit, the light emission unit aligned with the light receiving unit emits the light beam, and other light emission units not aligned with the light receiving unit do not emit any light beam.

3. The optical detection apparatus according to claim 1, wherein the sample comprises blood.

4. The optical detection apparatus according to claim 1, wherein the property measured by using the electrical signal comprises absorbance of the sample.

5. The optical detection apparatus according to claim 1, wherein each light emission unit comprises a light emitting diode (LED), a laser, or a xenon lamp.

6. The optical detection apparatus according to claim 1, wherein each light receiving unit comprises a photodiode, a photo-multiplier tube (PMT) or a charge-coupled device (CCD).

7. The optical detection apparatus according to claim 1, wherein the driving unit comprises a step motor, a servo motor, a linear motor, a DC brushless motor, a DC brush motor, or an induction motor.

8. An optical measurement system, comprising:
a carrier, having at least one accommodation groove, wherein the accommodation groove is capable of accommodating a sample; and
an optical detection apparatus, comprising:
a plurality of light emission units, each capable of emitting a light beam;
at least one light receiving unit, capable of receiving the light beam passing through the sample, and converting the light beam passing through the sample to an electrical signal;
a driving unit, capable of changing the relative position of each of the light emission units and the sample; and
an analyzing unit, electrically connected to the light receiving unit, and capable of measuring a property of the sample by using the electrical signal, wherein a number of the light receiving unit is less than a number of the light emission units,
wherein the light emission units are arranged into a straight line along a row direction, and the driving unit is capable of moving the light emission units back and forth along the row direction when positions of the sample and the light receiving unit are fixed.

9. An optical measurement system, comprising:
a carrier, having at least one accommodation groove, wherein the accommodation groove is capable of accommodating a sample; and
an optical detection apparatus, comprising:
a plurality of light emission units, each capable of emitting a light beam;
at least one light receiving unit, capable of receiving the light beam passing through the sample, and converting the light beam passing through the sample to an electrical signal;
a driving unit, capable of changing the relative position of each of the light emission units and the sample; and
an analyzing unit, electrically connected to the light receiving unit, and capable of measuring a property of the sample by using the electrical signal, wherein a number of the light receiving unit is less than a number of the light emission units, wherein when one of the light emission units is substantially aligned with the light receiving unit, the light emission unit aligned with the light receiving unit emits the light beam, and other light emission units not aligned with the light receiving unit do not emit any light beam.

10. The optical detection apparatus according to claim 9, wherein the light emission units are arranged into a straight line along a row direction, and the driving unit is capable of moving the light emission units back and forth along the row direction when positions of the sample and the light receiving unit are fixed.

11. The optical detection apparatus according to claim 9, wherein the light emission units are arranged into an annular shape, and the driving unit is capable of rotating the light emission units along the annular shape when positions of the sample and the light receiving unit are fixed.

* * * * *